(12) United States Patent
Wang

(10) Patent No.: US 7,919,239 B2
(45) Date of Patent: Apr. 5, 2011

(54) INCREASING HYBRIDIZATION EFFICIENCIES

(75) Inventor: Hui Wang, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 311 days.

(21) Appl. No.: 11/173,078

(22) Filed: Jul. 1, 2005

(65) Prior Publication Data

US 2007/0003937 A1    Jan. 4, 2007

(51) Int. Cl.
*C12Q 1/68* (2006.01)
*C12P 19/34* (2006.01)
*C12M 1/34* (2006.01)
*C12M 3/00* (2006.01)
*C07H 21/02* (2006.01)
*C07H 21/04* (2006.01)

(52) U.S. Cl. ..... 435/6; 435/91.3; 435/91.51; 435/287.2; 536/23.1; 536/24.3

(58) Field of Classification Search ............. 435/6, 91.3, 435/91.51, 87.2; 536/23.1, 24.3
See application file for complete search history.

(56) References Cited

U.S. PATENT DOCUMENTS

| | | |
|---|---|---|
| 2004/0110205 A1 | 6/2004 | Wang |
| 2005/0059019 A1 | 3/2005 | Bulow et al. |
| 2005/0074788 A1 | 4/2005 | Dahlberg et al. |
| 2005/0277139 A1* | 12/2005 | Bentwich et al. ............ 435/6 |
| 2008/0269072 A1* | 10/2008 | Hart et al. .................. 506/16 |

FOREIGN PATENT DOCUMENTS

WO    WO2006/047454    *    5/2006

OTHER PUBLICATIONS

Krichevsky et al , A microRNA array reveals extensive regulation of microRNAs during brain development, 2003, RNA, 9, 1274-1281.*
Liu et al, An oligonucleotide microchip for genome wide microRNA profiling in human and mouse tissues, 2004, PNAS, 101, 9740-9744, published Jun. 29, 2004.*
Ramakrishnan et al, An assessment of Motorola codelink microarray performance for gene expression profiling applications, 2002, 30, e30.*
Nelson et al, The microRNA world, small entity, 2003, Trends in Biochemical Science, 28, 534-540.*
miRNA-9 Tm brochure, printed Nov. 30, 2009, p. 1.*
miRNA-131 Tm brochure printed Nov. 30, 2009, p. 1.*
clamp definition brouchure, printed Dec. 2, 2009, p. 1.*
MicroRNAs and cancer, Michael T. McManus; Academic Press; Seminars in Cancer Biology 13 (2003) 253-258.
Human MicroRNA Targets, Bino John, Anton J. Enright, Alexei Aravin, Thomas Tuschl, Chris Sander, and Debora S. Marks; PLOS Biology; Nov. 2004, vol. 2, Issue 11, pp. 1862-1879.
Human microRNA genes are frequently located at fragile sites and genomic regions involved in cancers, George Adrian Calin et al.; PNAS; Mar. 2, 2004, vol. 101, No. 9, pp. 2999-3004.
An oligonucleotide microchip for genome-wide microRNA profiling in human and mouse tissue, Change-Gong Liu et al.; PNAS, Jun. 29, 2004, vol. 101, No. 26.
An oligonucleotide microarray for microRNA expression analysis based on labeling RNA with quantom analysis based on labeling RNA with quantum dot and nanogold probe, Ru-Qiang Liang, Wei Li, Yang Li, Cui-yan Tan, Jian-Xun Li, You-Xin Jin, and Kang-Cheng Ruan; Nudeic Acids Research, 2005, vol. 33, No. 2.
Microarray analysis of microRNA expression in the developing mammalian brain, Eric A. Miska, Ezequiel, Alvarez-Saavedra, Matthew Townsend, Akira Yoshii, Nenad Sestan, Pasko Rakic, Martha Constantine-Paton, and H Robert Horvitz; Genome Biology 2004, R:R68.
Liang, R., et al. An oligonucleotide microarray for microRNA expression analysis based on labeling RNA with quantum dot and nanogold probe. Nucleic Acids Research. 2005, vol. 33, No. 2, p. e17.
Nelson, P., et al. Microarray-based, high-throughput gene expression profiling of microRNAs. Nature Methods. 2004, vol. 1, No. 2, pp. 155-161.
Thomson, J.M., et al. A custom microarray platform for analysis of microRNA gene expression. Nature Methods. 2004, vol. 1, No. 1, pp. 47-53.

* cited by examiner

*Primary Examiner* — Stephen Kapushoc
*Assistant Examiner* — Narayan K Bhat

(57) ABSTRACT

Aspects of the disclosure are generally directed to probes and probe compositions for detecting or quantifying a target. One aspect provides a method for selectively hybridizing a probe to a polynucleotide by contacting a sample containing a first and second polynucleotide with a probe. The probe includes a number of nucleotides complementary to the first or second polynucleotide in the region of mismatch between the first and second polynucleotides. Another aspect provides arrays including the disclosed probes and methods of using the arrays and the probes.

8 Claims, 2 Drawing Sheets

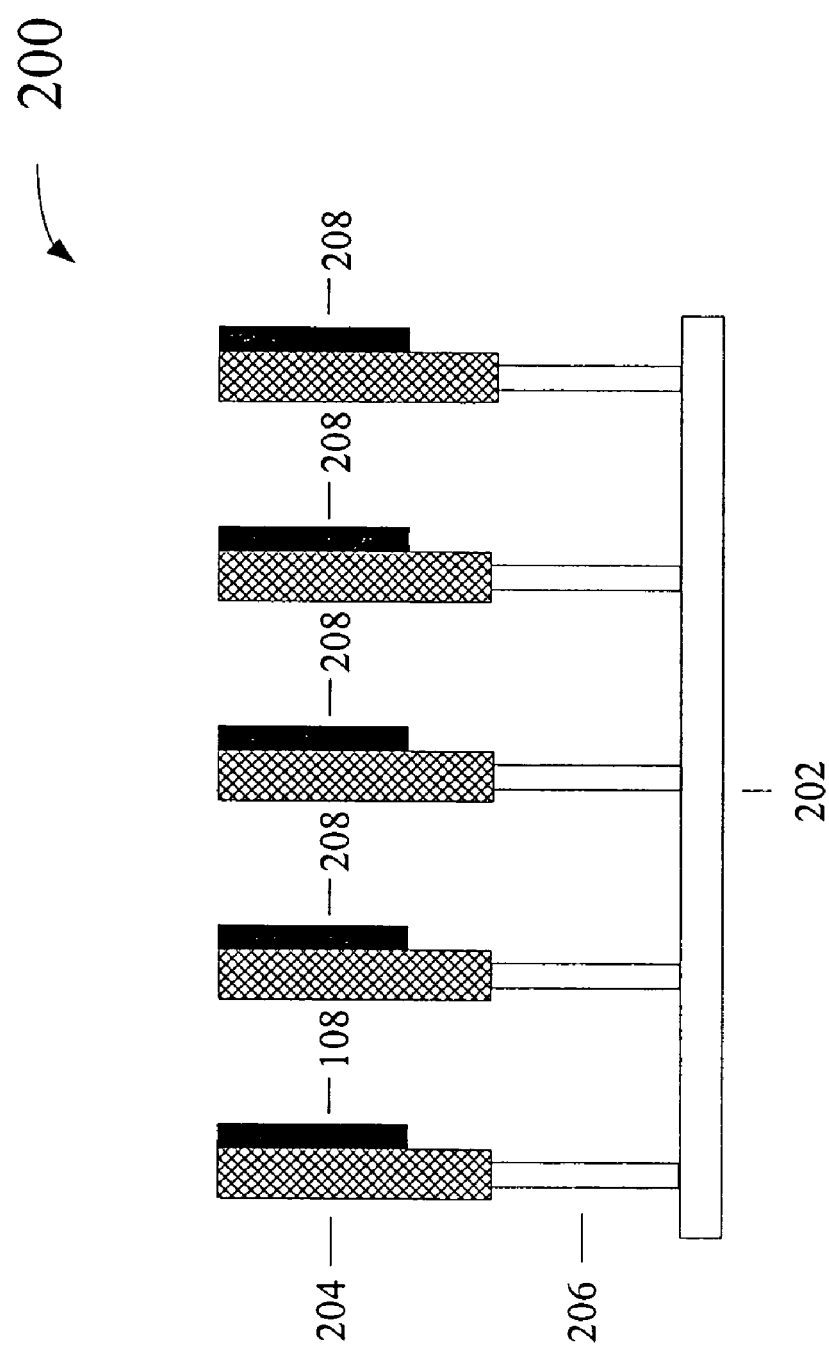

US 7,919,239 B2

INCREASING HYBRIDIZATION EFFICIENCIES

BACKGROUND OF THE INVENTION

Gene silencing by RNA molecules has been implicated in a wide variety of physiological pathways including pathologies such as cancer and the control of cell proliferation, cell death, fat metabolism, neuronal patterning, modulation of hematopoietic lineage differentiation, and control of leaf and flower development. Accordingly, there is increasing demand for methods for detecting and quantifying RNA molecules involved in gene regulation.

Conventional methods and standards for detecting and quantifying the presence of RNA molecules employ technologies such as gene chips or arrays. The presence of a specific RNA molecule can be detected when, for example, the target RNA molecule binds to a complementary sequence on an array. Small RNA molecules including microRNA (miRNA), tiny non-coding RNA (tncRNA), short interfering RNA (siRNA) and small modulatory RNA (smRNA) can be difficult to detect because of their size, copy number, and susceptibility to enzymatic degradation. The number of copies of such a small RNA present in a sample can be minuscule compared to the presence of other transcripts and the small RNA can be undetectable because of overwhelming signal from abundant non-target RNA transcripts.

SUMMARY

The present invention relates to methods for detecting or quantitating a small RNA, methods for detecting or quantitating binding to a nucleic acid array, the arrays, and probes that can be used in such methods and arrays.

In an embodiment, the present invention includes a method for detecting a small RNA, such as an miRNA. The method can include providing a first probe comprising consecutive nucleotides complementary to at least 12 consecutive nucleotides starting from about the 3' end of a small RNA, such as an miRNA. The method can also include contacting a sample suspected of containing the miRNA with the first probe and monitoring for detectable binding of the miRNA to the first probe.

In an embodiment, the present invention includes a probe. The probe can include consecutive nucleotides complementary to at least about 10 consecutive nucleotides starting from about the 3' end of a small RNA, such as an miRNA. The probe can also include heterologous nucleotides, such as a stilt for coupling the probe to a support. The consecutive nucleotides can be coupled to the heterologous nucleotides.

In an embodiment, the present invention includes an array. The array can include a polynucleotide comprising consecutive nucleotides complementary to at least about 10 consecutive nucleotides starting from about the 3' end of a small RNA, such as an miRNA. The polynucleotide can also include a linker. In the array, the polynucleotide is coupled to a substrate.

Another aspect relates to a computer program product for use with a method and apparatus such as described herein. The program product includes a computer readable storage medium having a computer program stored thereon and which, when loaded into a programmable processor, provides instructions to the processor of that apparatus such that it will execute the procedures required of it to perform a method of the present disclosure.

BRIEF DESCRIPTION OF THE FIGURES

FIG. 2 schematically illustrates an exemplary array.

DETAILED DESCRIPTION

Definitions

Figure 1:
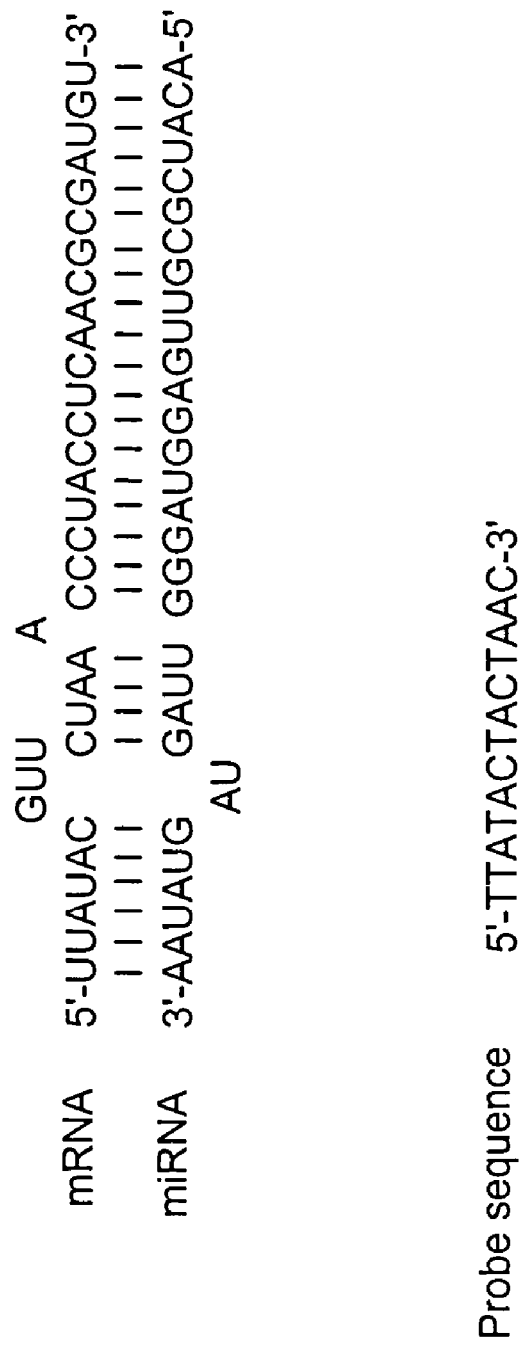
FIG. 1 shows an exemplary probe sequence and the incomplete hybridization between messenger RNA and miRNA.

In the present application, unless a contrary intention appears, the following terms refer to the indicated characteristics.

As used herein the phrase "small RNA" refers to an RNA including no more than about 100 nucleotides (e.g., no more than about 50 nucleotides, or no more than about 30 nucleotides). Small RNAs include: microRNA (miRNA), tiny non-coding RNA (tncRNA), short interfering RNA (siRNA), small modulatory RNA (smRNA), and the like, and mixtures thereof. Small RNA are smaller than messenger RNA. Messenger RNA generally contains many hundreds or thousands or nucleotides. In certain situations, many small RNA can bind to a single molecule of messenger RNA.

As used herein, the term "microRNA" or "miRNA" refers to a class of small noncoding RNAs. miRNA has been observed to contain, for example, about 20 to about 30 nucleotides (nt). miRNAs are single-stranded RNAs that can be produced from hairpin containing RNA molecules.

As used herein, the term "nucleic acid" refers to a polymer made up of nucleotides, e.g., deoxyribonucleotides or ribonucleotides.

As used herein, the terms "ribonucleic acid" and "RNA" refers to a polymer that includes at least one ribonucleotide, e.g., a polymer made up completely of ribonucleotides.

As used herein, the terms "deoxyribonucleic acid" and "DNA" refers to a polymer made up of deoxyribonucleotides.

As used herein, the term "polynucleotide" includes a nucleotide multimer having any number of nucleotides (for example 10 to 200, or more). This includes polynucleotides in which the conventional backbone has been replaced with a non-naturally occurring or synthetic backbone, as well as polynucleotides containing synthetic or non-naturally occurring nucleotides in which one or more of the conventional or canonical bases has been replaced with a group (natural or synthetic) capable of participating in Watson-Crick type hydrogen bonding interactions. Polynucleotides include single or multiple stranded configurations, where one or more of the strands may or may not be completely aligned with another. For example, a polynucleotide can include DNA (including cDNA), RNA, oligonucleotides, and PNA and other polynucleotides as described in U.S. Pat. No. 5,948,902 and references cited therein (all of which are incorporated herein by reference), regardless of the source.

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides.

An "oligonucleotide" generally refers to a nucleotide multimer of about 10 to 100 nucleotides in length.

As used herein, the phrases "percent (%) nucleic acid sequence identity" and "% nucleic acid sequence identity" used with respect to the target and the disclosed probes and arrays, or the complement thereof refers to the percentage of nucleotides in a sequence of interest or target that are identical with the nucleotides in the disclosed probes and arrays, or the complement thereof after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms. Sequence comparison programs including the publicly available NCBI-BLAST2 (Altschul et al., Nucleic Acids Res. 25:3389-3402 (1997)) can be employed for calculating % identity with its search parameters set to default values.

As used herein, the phrase "stringent conditions" or "high stringency conditions" for hybridization of oligo or polynucleotides include, for example: washing at low ionic strength and high temperature, e.g., 0.015 M sodium chloride/ 0.0015 M sodium citrate/0.1% sodium dodecyl sulfate at 50° C.; hybridization in the presence of a denaturing agent, e.g., 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or hybridizing in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), an random sequenced 25-mer as blocker, 0.1% SDS, and 10% dextran sulfate at 42° C. and washing at 42° C. in 0.2×SSC (sodium chloride/sodium citrate) and 50% formamide followed by washing with 0.1×SSC containing EDTA at 55° C.

"Hybridizing" and "binding", with respect to polynucleotides, are used interchangeably. "Hybridizing conditions" for a polynucleotide array refer to suitable conditions of time, temperature and the like, such that a target sequence present in solution will bind to an array feature carrying a complementary sequence to a greater extent than to features carrying only sequences which are not complementary to the target sequence (and preferably at least 20% or 100%, or even 200 or 500% greater).

As used herein, the term "isolated" polynucleotide refers to a polynucleotide that is identified and separated from at least one component of its natural environment. A recombinantly produced or synthetic polynucleotide is an isolated polynucleotide.

As used herein, the phrase "control sequences" refers to DNA sequences controlling transcription of an operably linked polynucleotide in a selected host cell or organism.

As used herein, the phrase "operably linked" refers to a polynucleotide in a functional relationship with another polynucleotide.

An "array", unless a contrary intention appears, includes any one-, two- or three-dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). Target probes may be covalently bound to a surface of a non-porous or porous substrate either directly or through a linker molecule, or may be adsorbed to a surface using intermediate layers (such as polylysine) or porous substrates.

An "array layout" refers to one or more characteristics of the array or the features on it. Such characteristics include one or more of: feature positioning on the substrate; one or more feature dimensions; some indication of an identity or function (for example, chemical or biological) of a moiety at a given location; how the array should be handled (for example, conditions under which the array is exposed to a sample, or array reading specifications or controls following sample exposure).

A "pulse jet" is a device which can dispense drops in the formation of an array. Pulse jets operate by delivering a pulse of pressure to liquid adjacent an outlet or orifice such that a drop will be dispensed therefrom (for example, by a piezoelectric or thermoelectric element positioned in a same chamber as the orifice).

An array "package" may be the array plus only a substrate on which the array is deposited, although the package may include other features (such as a housing with a chamber).

An "aptamer" generally refers to a double stranded DNA or single stranded RNA molecule that binds to specific molecular targets, such as a protein or metabolite.

A "chamber" references an enclosed volume (although a chamber may be accessible through one or more ports).

A "region" refers to any finite area, for example a finite area on the array that can be illuminated and any resulting fluorescence therefrom simultaneously (or shortly thereafter) detected, for example a pixel.

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station.

It will also be appreciated that throughout the present application, that words such as "top", "upper", and "lower" are used in a relative sense only.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference where permissible except insofar as they may conflict with those of the present application (in which case the present application prevails).

Methods of Detecting Small RNA

The present invention relates to methods for detecting or quantitating a small RNA, methods for detecting or quantitating binding to a nucleic acid array, the arrays, and probes that can be used in such methods and arrays.

In an embodiment, the present invention relates to a method for detecting a small RNA such as an miRNA. The method can include providing a probe including nucleotides complementary to nucleotides of the small RNA. For example, the probe can be complementary to consecutive nucleotides (e.g., about 10 consecutive nucleotides) of the small RNA, such as consecutive nucleotides at or near the 3' end of the small RNA. In an embodiment, the small RNA is an mRNA and the probe is complementary to at least about 10 consecutive nucleotides of the miRNA. The probe can be complementary to consecutive nucleotides starting at the 3' end of the small RNA, starting at the nucleotide adjacent to the 3' nucleotide (the second nucleotide from the 3' end), at the third nucleotide from the 3' end, at the fourth nucleotide from the 3' end, at the fifth nucleotide from the 3' end, or at the sixth nucleotide from the 3' end. In other words, in certain embodiments, the method can employ a probe for binding to small RNA omits (does not include) a sequence complementary to a portion of the small RNA, wherein the portion consists of the 3'-terminal 1, 2, 3, 4, 5, or 6 nucleotides of the small RNA.

The probe can include any number of nucleotides suitable for binding to the small RNA. For example, in an embodiment, the probe can include about 10 to about 30 (e.g., 32) consecutive nucleotides complementary to consecutive nucleotides of the small RNA. In an embodiment, the probe can include about 12 to about 25 consecutive nucleotides complementary to consecutive nucleotides of the small RNA. In an embodiment, the probe can include about 12 to about 18 consecutive nucleotides complementary to consecutive nucleotides of the small RNA. In an embodiment, the method employs a probe including at least 6, at least 7, or at least 12 consecutive nucleotides complementary to consecutive nucleotides starting from the 3' end of an miRNA.

One or more of the probes can be coupled to a support, such as a solid support. The probe that can bind to a small RNA can be called a first probe.

The method can include employing the probe in any of a variety of situations in which the probe can bind to a small RNA. For example, the method can include contacting a sample suspected of containing the small RNA with the probe. Such a method can also include monitoring for binding of the small RNA to the probe. Monitoring for binding can employ an apparatus suitable for detecting binding that occurs. Should binding occur, the method can include detecting binding of the small RNA to the array.

The method can employ a plurality of probes that can bind to small RNA. Each individual probe can have the characteristics described above with respect to the present invention. The plurality of probes can include probes with different nucleic acid sequences. The different probes can be complementary to different small RNAs. In an embodiment, a probe of a particular sequence is complementary to a particular small RNA. In an embodiment, a plurality of probes each having a particular sequence are complementary to a plurality of particular small RNAs. In an embodiment, at least two of the plurality of probes include distinct sequences of nucleotides. A plurality of probes can be coupled to the support in an array format.

The method can employ a plurality of probes that can bind to small RNA in a variety of amounts. Consider, for example, a method employing a first probe complementary to a first miRNA and a first probe complementary to a second miRNA. Such a method can employ the two probes in unequal amounts. For example, if a sample is suspected to contain the first miRNA in a 10,000 fold molar excess over the second miRNA, the method can employ 10 probes complementary to the first miRNA (or features containing probes complementary to the first miRNA) for each probe or feature including probes complementary to the second miRNA. In an embodiment, the amounts of each first probe are proportional to an expected relative amount of first and second miRNA in a sample.

By way of further example, a method can include one or more first probes in greater amounts. For example, certain miRNA sequences have a high propensity for cross hybridization. For such miRNAs, the present method can include a greater number first probes that can hybridize to this miRNA. Although not limiting to the present invention, it is believed that such a greater quantity can reduce cross hybridization.

One embodiment provides an array having features in about the same stoichiometric ratio as target small RNAs in a sample. For example, if relative stoichiometric information is available for some or all of the small RNAs (e.g., miRNAs) and their corresponding target messenger RNAs in a sample, specific arrays can be designed to interrogate the relative or even absolute quantities of various targets. In an embodiment, prior quantitative information for target polynucleotides can be obtained prior to producing the disclosed arrays. For example, T4 RNA ligase can be used for quantitative labeling for all RNA species in a sample.

Methods Including Probes for Large RNA

In an embodiment, the present method can also employ a probe selected to be complementary to a large RNA, which can be referred to as a probe for large RNA. For example, the probe can include nucleotides complementary to messenger RNA. Such a probe can be referred to as a probe for messenger RNA. The method can also include monitoring for binding of messenger RNA to the probe for messenger RNA. A probe for messenger RNA can include any number of nucleotides suitable for binding to the messenger RNA. For example, the probe can include about 12 to about 25 (e.g., 24) nucleotides complementary to nucleotides of the messenger RNA. One or more of the probes for messenger RNA can be coupled to a support, such as a solid support.

The method can include employing the probe for messenger RNA in any of a variety of situations in which the probe can bind to a messenger RNA. For example, the method can include contacting a sample suspected of containing a small RNA and a messenger RNA with the probe. Such a method can also include monitoring for binding of the messenger RNA to the probe for messenger RNA. Monitoring for binding can employ an apparatus suitable for detecting binding that occurs. Should binding occur, the method can include detecting binding of the messenger RNA to the array.

The method can employ a plurality of probes that can bind to messenger RNA. The plurality of probes can include probes with different nucleic acid sequences. The different probes can be complementary to different messenger RNAs. In an embodiment, a probe of a particular sequence is complementary to a particular messenger RNA. In an embodiment, a plurality of probes for messenger RNA each having a particular sequence are complementary to a plurality of particular messenger RNAs. In an embodiment, at least two of the plurality of probes for messenger RNA include distinct sequences of nucleotides. A plurality of probes for messenger RNA can be coupled to the support in an array format.

In an embodiment, the probes can be in the form of an array system. For example, the array system can include a plurality of first probes that can bind miRNA and a plurality of probes for messenger RNA that can bind messenger RNA. Although not limiting to the present invention, hybridization of the first probe to the miRNA can be kinetically and/or thermodynamically favored over hybridization of an miRNA to its target messenger RNA. In an embodiment, such an array system can detect and/or quantify both the miRNA and the messenger RNA. In an embodiment, the method and system need not include purifying or amplifying polynucleotide test samples. The system can include a plurality of arrays.

Probes for Small RNA

The present invention relates to probes suitable for binding (e.g., selective binding) to small RNA. Such a probe can include nucleotides complementary to nucleotides of the small RNA. For example, the probe can be complementary to consecutive nucleotides of the small RNA, such as consecutive nucleotides at or near the 3' end of the small RNA. In an embodiment, the small RNA is an miRNA and the probe is complementary to at least about 10 consecutive nucleotides of the miRNA. The probe can be complementary to consecutive nucleotides starting at the 3' end of the small RNA, starting at the nucleotide adjacent to the 3' nucleotide (the second nucleotide from the 3' end), at the third nucleotide from the 3' end, at the fourth nucleotide from the 3' end, at the fifth nucleotide from the 3' end, or from the sixth nucleotide from the 3' end. In other words, in certain embodiments, a probe for binding to small RNA omits (does not include) a sequence complementary to a portion of the small RNA, wherein the portion consists of the 3'-terminal 1, 2, 3, 4, 5, or 6 nucleotides of the small RNA.

The probe can include any number of nucleotides suitable for binding to the small RNA. For example, in an embodiment, the probe can include about 10 to about 30 (e.g., 32) consecutive nucleotides complementary to consecutive nucleotides of the small RNA. In an embodiment, the probe can include about 12 to about 25 consecutive nucleotides complementary to consecutive nucleotides of the small RNA. In an embodiment, the probe can include about 12 to about 18 consecutive nucleotides complementary to consecutive nucleotides of the small RNA. In an embodiment, the probe includes at least 6, at least 7, or at least 12 consecutive nucleotides complementary to consecutive nucleotides starting from the 3' end of an miRNA.

The probe can also include a heterologous polynucleotide. The heterologous polynucleotide can include a number of nucleotides effective to, for example, couple the probe to a support. In an embodiment, the heterologous polynucleotide can include about 10 to about 100 nucleotides, about 10 to about 60 nucleotides, or about 10 to about 30 nucleotides. The heterologous nucleotides can be coupled to the consecutive nucleotides that are complementary to the small RNA. In an embodiment, the heterologous polynucleotide can include a "stilt" polynucleotide. The stilt polynucleotide can be configured to couple the complementary nucleotides to a support. Such heterologous nucleotide may include a nucleotide clamp sequence or a hairpin such as is described in copending application Ser. No. 11/173,693 filed evendate herewith.

The present probe can be a component of an array. The array can include the present probe coupled to a substrate. In an embodiment, the array can include a plurality of probes that can bind to small RNA in a variety of amounts. Consider, for example, an array including a first probe complementary to a first miRNA and a first probe complementary to a second miRNA. Such an array can include the two probes in unequal amounts. For example, if a sample is suspected to contain the first miRNA in a 10,000 fold molar excess over the second miRNA, the array can include 10 probes complementary to the first miRNA (or features containing probes complementary to the first miRNA) for each probe or feature including probes complementary to the second miRNA. In an embodiment, the amounts of each first probe are proportional to an expected relative amount of first and second miRNA in a sample.

Embodiments of the Present Methods and Probes

FIG. 1 illustrates an miRNA (miRNA 108, SEQ ID NO:1) and a sequence from its target messenger RNA (SEQ ID NO:2). Notably, in this illustrated example, the 3' end of the miRNA has mismatches compared to the messenger RNA (and vice versa). A probe for this illustrated miRNA could base pair with (complement) only with a sequence of the miRNA at its 3' end, for example, 5'-GUUAGUAGUAUAA-3' (SEQ ID NO:3). Such probe would have no mismatches with the miRNA and would have the sequence shown in FIG. 1, 5'-TTATACTACTAAC-3' (SEQ ID NO:4).

Although not limiting to the present invention, it is believed that many miRNAs may have a 3' end with less complementary base pairing with its target miRNA than the 5' end of the miRNA. For example, the inventors have determined that most known miRNAs have high sequence complementarity with their target messenger RNA for the first eight 5' nucleotides of the miRNA. For such an miRNA, the 3' end of the miRNA is more susceptible to binding to a probe having about 10 (e.g., 8) or more consecutive base pairing nucleotides for the 3' end of the miRNA. Although not limiting to the present invention, it is believed that such a probe provides more effective strand invasion by the probe against any potential miRNA-miRNA imperfect duplex in the complex sample mixture.

Although not limiting to the present invention, it is believed that in embodiments in which the target miRNA does not completely hybridize to its respective miRNA and the probe does completely hybridize to the miRNA, the probe-miRNA duplexes are thermodynamically favored over (i.e., more stable than) miRNA-miRNA duplexes. In such an embodiment, the first probe can contain an effective number of consecutive nucleotides complementary to the miRNA including part or all of a region of incomplete hybridization between the miRNA and miRNA sufficient for the probe to selectively or preferentially hybridize to the miRNA in the presence of the miRNA. Similarly, a probe for messenger RNA can be designed to permit the probe for messenger RNA to specifically or preferentially hybridize to the miRNA including part or all of the region of mismatch between the miRNA and the miRNA or excluding the region of mismatch between the miRNA and miRNA.

In an embodiment, a first probe includes a hybridization sequence in which each base of the hybridization sequence base pairs with its complementary base in the miRNA. For example, the consecutive nucleotides of the probe can hybridize to consecutive nucleotides of the miRNA. In an embodiment, consecutive nucleotides of the probe can hybridize to consecutive bases of the miRNA at sequences in which the miRNA has nucleotides that do not hybridize to its target messenger RNA, in which the target messenger RNA has nucleotides that do not hybridize to the miRNA, or both. Although not limiting to the present invention, it is believed that an entire probe that hybridizes to consecutive nucleotides of the miRNA without mismatches can be kinetically and/or thermodynamically favored over hybridization with the target messenger RNA.

In certain embodiments, the duplex formed between the disclosed probes and the 3' end of the miRNA is longer, for example by 1, 2, 3, 4, 5, 6, 7, 8, 9, or more nucleotides, than the completely complementary region of miRNA-miRNA duplex. In an embodiment, such a probe can provide a duplex thermodynamically more stable than the duplex formed between the 5' end of the miRNA and the 3' end of the miRNA.

FIG. 2 schematically illustrates an exemplary array system 200. Probes 204 are bound or attached to substrate 202 by a linker or stilt sequence 106. For example, the 5' end of the probe can be bound to the linker or stilt sequence which in turn is bound to the substrate. The linker or stilt sequence is typically a polymer that does not interact or hybridize with the one or more targets. A suitable linker or stilt sequence can include, for example, 6 to 12 nucleotides. It will be appreciated that any number of monomers can be used in the linker or stilt sequence to optimize interaction of the probes with targets in a sample. In one embodiment, the probes are releasably attached to substrate 202 or to the linker or stilt sequence. In another embodiment, the probes are bound to the linker, stilt sequence, or substrate by a photocleavable bond or a reducible bond such as a disulfide bridge. In still another embodiment, the linker or stilt sequence includes a cleavage site or photolabile bond that can be severed to release the probe and at least a part of the linker or stilt sequence. The cleavage site can be a chemically cleavable site or a site recognized by an enzyme such as a peptidase or nuclease. In an embodiment, probes 204 each have a melting temperature in a predetermined range, for example about 50° C. to about 60° C. for one or more target miRNAs 208.

In certain embodiments, the samples used with the disclosed methods and compositions do not require amplification or purification prior to contact with the disclosed probes.

Melting Temperatures

One embodiment provides a method using the disclosed probes in which each probe is specific for a target and has a melting temperature for their respective target within about 15° C., typically within about 10° C., even more typically within about 5° C. of each other. Generally, one or more probes optionally having different sequences of monomers or a different number of monomers are selected based on their melting temperatures for their respective targets. In one embodiment, the probes typically have melting points for their targets in the range of about 50° to about 60° C. Probes can have different monomer sequences as well as different numbers of monomers but selected probes will each have a melting temperature for their respective targets within about 15° C., typically within about 10° C., even more typically within about 5° C. of each other. Probes specific for different targets also can have different sequences and different numbers of monomers provided they each have a melting temperature for their respective targets of within about 15° C., typically within about 10° C., even more typically within about 5° C. of each other. The probes are generally DNA, but can also include RNA, or can be a combination of RNA and DNA. The targets or probes are naturally occurring or non-naturally occurring polymers including, but not limited to nucleic acids such as RNA, DNA, PNA, polypeptides, and combinations thereof.

In an embodiment, an array includes probes and every one of the probes has a melting temperature for their respective target within about 15° C., within about 10° C., or within about 5° C. of each other. In an embodiment, all of the probes in the array have melting points for their targets in the range of about 50° to about 60° C. In an embodiment, an array includes probes and 80% of the probes have a melting temperature for their respective target within about 15° C., within about 10° C., or within about 5° C. of each other. In an embodiment, 80% of the probes in the array have melting points for their targets in the range of about 50° to about 60° C.

One embodiment provides determining the melting temperature of one or more probes for one or more targets. Representative probes are polymers including, but not limited to polymers of a single monomer (homopolymers) or polymers of more than one monomer (heteropolymers). Monomers can be non-naturally occurring or naturally occurring monomers such as deoxyribonucleotides, ribonucleotides, amino acids, sugars, carbon atoms, or derivatives thereof. The transition of double-stranded to single-stranded conformation can be monitored as an increase in absorbance and is marked by a sharp change in the extinction coefficient at the temperature where the conformational transition takes place. The temperature corresponding to the midpoint of the absorbance rise is called the melting temperature ($T_m$). In structural terms, $T_m$ is the temperature at which 50% of the base pairs in the duplex have been denatured. Methods for determining the melting temperature of nucleic acid duplexes are known in the art. See for example, Sambrook and Russell (2001) Molecular Cloning: A Laboratory Handbook, 10.38-10.41 and 10.47, which is incorporated by reference in its entirety.

$T_m$ can be determined mathematically using equations and algorithms known in the art. For duplex oligonucleotides shorter than 25 bp, "The Wallace Rule" can be used in which:

$$T_m(\text{in } °C.)=2(A+T)+4(C+G), \text{ where}$$

(A+T)—the sum of the A and T residues in the oligonucleotide, (C+G)—the sum of G and C residues in the oligonucleotide (Wallace, R. B., et al., Hybridization of synthetic oligodeoxyribonucleotides to phiX174 DNA: the effect of single base pair mismatch, Nucleic Acids Res., 6, 3543-3557, 1979). Computer programs for estimating $T_m$ are also available (Nicolas Le Novere (2001), MELTING, computing the melting temperature of nucleic acid duplex. Bioinformatics 17(12), 1226-1227). VisualOmp (DNA Software, Inc., Ann Arbor, Mich.) is an example of commercially available software for calculating probe:target duplex melting temperature.

$T_m$ can also be determined empirically using methods known in the art (Sambrook and Russell (2001) Molecular Cloning: A Laboratory Handbook, 10.38-10.41) Generally, one strand of a duplex is labeled with a detectable label, typically on the 3' end of the target. The unlabeled strand or probe is typically bound to a solid support. The labeled and unlabeled strands are brought into contact under various conditions and temperatures. The melting temperature can be determined by monitoring the amount of label that hybridizes to the bound unlabeled strand as a function of the hybridization temperature. Detectable label on the solid support indicates the presence of a duplex. As the hybridization temperature increases, more label is eluted from the solid support.

Methods Employing Arrays or the Present Probes

An exemplary method includes contacting such an array with a plurality of disclosed probes and arrays. Contacting can include any of a variety of known methods for contacting an array with a reagent, sample, or composition. For example, the method can include placing the array in a container and submersing the array in or covering the array with the reagent, sample, or composition. The method can include placing the array in a container and pouring, pipetting, or otherwise dispensing the reagent, sample, or composition onto features on the array. Alternatively, the method can include dispensing the reagent, sample, or composition onto features of the array, with the array being in or on any suitable rack, surface, or the like.

The present method can include contacting the nucleic acid array with a sample suspected of containing a polynucleotide that can bind to a feature on the array. The sample polynucleotide can include, for example, a gene, a transcript of the gene, a polynucleotide including a sequence from the gene, or a complement thereof. The method can include binding of the sample polynucleotide to a nucleic acid in a feature at a location on the array. Monitoring for binding can employ an apparatus suitable for detecting binding that occurs. Should binding occur, the method can include detecting binding of the sample polynucleotide to the array.

In an embodiment, the present method can include contacting the nucleic acid array with a sample including a plurality of sample polynucleotides. At least one, or all, of the sample polynucleotides can be capable of or suspected of being capable of binding to one or more features on the array. The plurality of sample polynucleotides can each be from the same cell, tissue, or organism. The plurality of sample polynucleotides can include polynucleotides of interest, for example, with respect to development, disease, or disorder of the cell, tissue, or organism. At least one, or all, of the sample polynucleotides can include a detectable label, for example, a second detectable label.

In an embodiment, the present method can include detecting a first detectable signal (e.g., color) from a standard polynucleotide and a second detectable signal from a sample polynucleotide. The method can include comparing the strength of the first and second detectable signals. Quantitating the sample polynucleotide can be based on this comparison.

Detecting can include any of a variety of known methods for detecting a detectable signal from a feature or location of an array. Any of a variety of known, commercially available apparatus designed for detecting signals of or from an array can be employed in the present method. Such an apparatus or method can detect one or more of the detectable labels described hereinbelow. For example, known and commercially available apparatus can detect colorimetric, fluorescent, or like detectable signals of an array. Surface plasmon resonance can be employed to detect binding of a disclosed probes and arrays to the array. The methods and systems for detecting a signal from a feature or location of an array can be employed for monitoring or scanning the array for any binding that occurs and results in a detectable signal. Monitoring or detecting can include viewing (e.g., visual inspection) of the array by a person.

The present disclosed probes and arrays or compositions can be provided in any variety of common formats. The present nucleotide or composition can be provided in a container, for example, as a solid (e.g., a lyophilized solid) or a liquid. In an embodiment, each of a plurality of disclosed probes and arrays is provided in its own container (e.g., vial, tube, or well). The present disclosed probes and arrays or compositions can be provided with materials for creating a nucleic acid array or with a complete nucleic acid array. In fact, the present polynucleotide or composition can be provided bound to one or more features of a nucleic acid array.

Another embodiment provides a method for obtaining miRNA and messenger RNA profiles of a sample using the same or different arrays. miRNA profiles and messenger RNA profiles can be quantitatively measured to determine the level of messenger RNA regulation by a specific miRNAs. Probes specific for miRNA can be used with probes specific for messenger RNA as disclosed above to specifically hybridize the probe to its respective target. The profiles can be obtained simultaneously, concurrently, contemporaneously, in parallel, or in series.

Target Profiling

Another embodiment provides a method for obtaining a profile of one or more targets, for example nucleic acids such as miRNA and/or the miRNA's target messenger RNA present in a sample. An expression profile for one or more target nucleic acids can be obtained by interrogating a sample with an array including probes specific for one or more miRNAs and/or their messenger RNA targets. In some embodiments, the base pairing regions of the probes are less than about 23 nt and specifically hybridize to a target in a sequence dependent manner. The probe can bind to one or more regions of one target nucleic acid or can bind to the same region present in multiple targets. Detection of probe:target hybridization indicates the expression or presence of a particular target or set of targets in the sample. The profile of a target can be correlated with pathologies such as cancer and the control of cell proliferation, cell death, fat metabolism, neuronal patterning, modulation of hematopoietic lineage differentiation, and control of leaf and flower development.

An exemplary array employed in the present method can include a plurality of locations. A plurality of these locations can include a feature that can bind a target polynucleotide. For example, a feature can bind a gene or genomic nucleic acids corresponding to a gene, a transcript of the gene, a polynucleotide including a sequence from the gene, a fragment of a target gene or transcript, or a complement thereof. The feature can include an oligonucleotide, polynucleotide, aptamer, polypeptide, or combinations thereof.

Detectable Labels

The present disclosed probes, arrays or targets can include a detectable label, for example, a first detectable label. Sample polynucleotides can include a detectable label, for example, a second detectable label. Suitable labels include radioactive labels and non-radioactive labels, directly detectable and indirectly detectable labels, and the like. Directly detectable labels provide a directly detectable signal without interaction with one or more additional chemical agents. Suitable of directly detectable labels include colorimetric labels, fluorescent labels, and the like. Indirectly detectable labels interact with one or more additional members to provide a detectable signal. Suitable indirect labels include a ligand for a labeled antibody and the like.

Suitable fluorescent labels include any of the variety of fluorescent labels disclosed in United States Patent Application Publication No. 20010009762, the disclosure of which is incorporated herein by reference. Specific suitable fluorescent labels include: xanthene dyes, e.g., fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g., Cy3, Cy5 and Cy7 dyes; alexa dyes, e.g., alexa fluor 555, alexa fluor 594; coumarins, e.g., umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes.

Methods of Making Probes and Probe Compositions

The present disclosed probes and arrays can be produced by known methods. For example, the disclosed probes and arrays can be made by known methods for chemical synthesis. Chemical synthesis can employ commercial synthesizers. Chemical synthesis can produce thousands or more different sequences in multi-well plates. The method can include synthesizing segments of the polynucleotide and ligating the segments to form the polynucleotide. Chemical synthesis can be employed to make a transcript or fragment thereof.

The disclosed probes and arrays can be made by known recombinant methods. For example, conventional cloning and subcloning techniques and PCR can be employed to produce the disclosed probes and arrays. In an embodiment, targets or fragments such as exons can be isolated from biological samples by PCR.

Recombinant Methods

DNA encoding genes or fragments of interest can be obtained from a suitable cDNA or genomic library. The libraries can be screened with probes designed to identify the exon of interest according to standard procedures. See, e.g., Sambrook et al., Molecular Cloning: A Laboratory Manual (New York: Cold Spring Harbor Laboratory Press, 2001). The probe can be labeled according to known methods so that it can be detected upon hybridization to DNA in the library. The binding regions of an miRNA to its messenger RNA can be isolated and ligated using known methods so that non-complementary regions of the miRNA are deleted or reduced in number. Alternatively, the probe may contain multiples of an miRNA binding region for a specific messenger RNA.

Host cells can be modified to produce the disclosed probes and arrays by transfecting or transforming with a cloning vector according to known techniques. The transfecting or transformed cells can be cultured in conventional nutrient media, which can be modified inducing promoters, selecting transformants, or amplifying the genes encoding the desired sequences. Suitable culture conditions (e.g., media, temperature, pH) can be chosen without undue experimentation. Suitable techniques for cell culture are known. See, e.g., Mammalian Cell Biotechnology: a Practical Approach, M. Butler, ed. (IRL Press, 1991) and Sambrook et al., supra.

Transfection can employ known methods appropriate for each host cell type. Suitable methods include $CaCl_2$, $CaPO_4$, liposome-mediated, or electroporation. Other known methods for introducing DNA into cells can be used. Suitable host cells for cloning or expressing DNA in vectors include prokaryote (e.g., E. coli), filamentous fungi or yeast, or higher eukaryote (e.g., insect or mammalian) cells. Such host cells are well-known and are publicly and even commercially available.

The DNA encoding the disclosed probes and arrays can be inserted into a replicable vector for amplification of the DNA. Suitable vectors are well-known and are publicly and even commercially available. The vector can, for example, be in the form of a plasmid, cosmid, virus particle, or phage. The appropriate nucleic acid sequence may be inserted into the vector by any of a variety of known procedures. The vector can also include, for example, a signal sequence, an origin of replication, a marker gene, an enhancer element, a promoter, and/or a transcription termination sequence. Such elements and sequences are known. The vector can be constructed employing well-known techniques. Gene amplification can be detected or measured in a host cell or other system by any of a variety of known methods (e.g., Southern blotting, Northern blotting, dot blotting, or in situ hybridization).

Arrays

In certain embodiments, the disclosed probes can be integrated into a diagnostic device, for example an array. The device can be interrogated with a sample to detect the presence and/or amount of one or more targets in the sample. The target or amount of target can then be correlated with a phenotype, for example, propensity to develop a pathology such as cancer. The presence, absence, or quantity of a detected or undetected target or combination of targets can be indicative of a phenotype of the source organism of the sample. More particularly, the disclosed device can be used to detect one or more targets present in a fluid sample including, but not limited to blood, serum, plasma, saliva, sweat, tears, mucous, stool, lymphatic fluid, semen, interstitial fluid, gastric fluid, spinal fluid, or a particular cell, cell type, a plurality of cell types, organism or individual, species, genus, order, or the like. For example, the probes can detect the presence or expression level of a gene or gene transcript or a polypeptide. The target can be found in a particular cell, microorganisms, virus, plant, fungus, eukaryote, prokaryote, or other organism.

In certain embodiments, the disclosed probes and arrays can be diagnostic of a particular growth condition, environmental condition, developmental stage, or the like. For example, the disclosed probes and arrays can be diagnostic of a gene of interest, in particular a miRNA gene of interest, in a particular developmental stage of an organism such as an insect larvae, seed, plant, or vertebrate fetus, typically a non-human vertebrate fetus.

Arrays on a substrate can be designed for testing against any type of sample, whether a trial sample, reference sample, a combination of them, or a known mixture of polynucleotides (in which latter case the arrays may be composed of features carrying unknown sequences to be evaluated). Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 50 cm$^2$, 20 cm$^2$, or even less than 10 cm$^2$, or less than 1 cm$^2$. For example, features may have widths (that is, diameter, for a round spot) in the range from a 10 μm to 1.0 cm. In other embodiments each feature may have a width in the range of 1.0 μm to 1.0 mm, of 5.0 μm to 500 μm, or of 10 μm to 200 μm. Non-round features may have area ranges equivalent to that of circular features with the foregoing width (diameter) ranges. Feature sizes can be adjusted as desired, for example by using one or a desired number of pulses from a pulse jet to provide the desired final spot size.

Substrates of the arrays can be any solid support, a colloid, gel or suspension. Exemplary solid supports include, but are not limited to metal, metal alloys, glass, natural polymers, non-natural polymers, plastic, elastomers, thermoplastics, pins, beads, fibers, membranes, or combinations thereof.

At least some, or all, of the features are of different compositions (for example, when any repeats of each feature composition are excluded the remaining features may account for at least 5%, 10%, or 20% of the total number of features), each feature typically being of a homogeneous composition within the feature. Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Array features will generally be arranged in a regular pattern (for example, rows and columns). However other arrangements of the features can be used where the user has, or is provided with, some means (for example, through an array identifier on the array substrate) of being able to ascertain at least information on the array layout (for example, any one or more of feature composition, location, size, performance characteristics in terms of significance in variations of binding patterns with different samples, or the like). Each array feature is generally of a homogeneous composition.

Each array may cover an area of less than 100 cm$^2$, or even less than 50 cm$^2$, 10 cm$^2$, or 1 cm$^2$. In many embodiments, the substrate carrying the one or more arrays will be shaped generally as a rectangular solid (although other shapes are possible), having a length of more than 4 mm and less than 1 m, for example, more than 4 mm and less than 600 mm, less than 400 mm, or less than 100 mm; a width of more than 4 mm and less than 1 m, for example, less than 500 mm, less than 400 mm, less than 100 mm, or 50 mm; and a thickness of more than 0.01 mm and less than 5.0 mm, for example, more than 0.1 mm and less than 2 mm, or more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, U.S. Pat. No. 6,656,740; 6,458,583; 6,323,043; 6,372,483; 6,242,266; 6,232,072; 6,180,351; 6,171,797; or 6,323,043; or in U.S. patent application Ser. No. 09/302,898 filed Apr. 30, 1999 by Caren et al., and the references cited therein. These references are incorporated herein by reference. Other drop deposition methods can also be used for fabrication. Also, instead of drop deposition methods, known photolithographic array fabrication methods may be used. Interfeature areas need not be present particularly when the arrays are made by photolithographic methods as described in those patents.

Methods Employing Arrays

Following receipt by a user of an array made by an apparatus or method of the present disclosure, it will typically be exposed to a sample (for example, a fluorescently labeled polynucleotide or protein containing sample) in any well known manner and the array is then read. Reading of the array may be accomplished by illuminating the array and reading the location and intensity of resulting fluorescence at multiple regions on each feature of the array. For example, a scanner may be used for this purpose which is similar to the AGILENT MICROARRAY SCANNER manufactured by Agilent Technologies, Palo Alto, Calif. Other suitable apparatus and methods are described in U.S. patent applications: Ser. No. 10/087,447 "Reading Dry Chemical Arrays Through The Substrate" by Corson et al.; and in U.S. Pat. Nos. 6,592,036; 6,583,424; 6,486,457; 6,406,849; 6,371,370; 6,355,921; 6,320,196; 6,251,685; and 6,222,664. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,251,685, or 6,221,583 and elsewhere). Data from read arrays may be processed in any know manner, such as described in U.S. Pat. No. 6,591,196, U.S. patent application Ser. No. 09/659,415 filed Sep. 11, 2000 for "Method And System For Extracting Data From Surface Array Deposited Features", and many commercially available array feature extraction software packages. A result obtained from the reading followed by a method of the present invention may be used in that form or may be further processed to generate a result such as that obtained by forming conclusions based on the pattern read from the array (such as whether or not a particular target sequence may have been present in the sample, or whether or not a pattern indicates a particular condition of an organism from which the sample came). A result of the reading (whether further processed or not) may be forwarded (such as by communication) to a remote location if desired, and received there for further use (such as further processing).

In one embodiment the array can be read using Matrix Assisted Laser Desorption Ionization Time-of-flight Mass Spectrometry (MALDI).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The disclosed subject matter has been described with reference to various specific and preferred embodiments and techniques. However, it should be understood that many variations and modifications may be made while remaining within the spirit and scope of the disclosure.

What is claimed is:

1. A method comprising:
   a) contacting a sample comprising a plurality of labeled miRNA molecules with an array of probes, each of which probes is:
      i. bound to a substrate
      ii. complementary to said labeled miRNA molecules starting at the 3' terminal nucleotide of said labeled miRNA molecules, to produce a plurality of duplexes between said probes and said labeled miRNA molecules,
      wherein said plurality of duplexes comprises:
         first duplexes in which the 5' end of said labeled miRNA molecules is hybridized with said probe and
         second duplexes in which the 5' end of said labeled miRNA molecules is not hybridized with said probe, and
      wherein the melting temperatures of said duplexes are within 15° C. of each other; and
   b) detecting binding of said miRNA molecules with each of said probes.

2. The method of claim 1, wherein binding of said labeled miRNA to each of said probes forms a duplex that is longer by 1, 2, 3, 4, 5, 6, 7, 8, 9, or more nucleotides than the complementary region formed between said labeled miRNA and its respective target.

3. The method of claim 1, wherein said melting temperatures of said duplexes are within 5° C. of each other.

4. The method of claim 1, wherein each probe of said array comprises 10 to 32 nucleotides that are complementary to said labeled miRNA molecules.

5. The method of claim 1, wherein said each probe of said array comprises at least 10 consecutive nucleotides that are complementary to said miRNA.

6. The method of claim 1, wherein the number of said probes on said array is proportional to the expected relative amount of said labeled miRNA molecules in said sample.

7. The method of claim 1, wherein each probe of said array is complementary to a different labeled miRNA molecules in said sample.

8. The method of claim 1, wherein each of said probes comprises a nucleotide clamp coupled to consecutive nucleotides complementary to said miRNA.

* * * * *

UNITED STATES PATENT AND TRADEMARK OFFICE
CERTIFICATE OF CORRECTION

PATENT NO. : 7,919,239 B2
APPLICATION NO. : 11/173078
DATED : April 5, 2011
INVENTOR(S) : Hui Wang It is certified that error appears in the above-identified patent and that said Letters Patent is hereby corrected as shown below:

On the face page, in field (56), under "Other Publications", in column 1, line 1, delete "al ," and insert -- al., --, therefor.

On the face page, in field (56), under "Other Publications", in column 2, line 5, delete "clamp" and insert -- Clamp --, therefor.

On the face page, in field (56), under "Other Publications", in column 2, line 5, delete "brouchure," and insert -- brochure, --, therefor.

On the face page, in field (56), under "Other Publications", in column 2, line 21, delete "Nudeic" and insert -- Nucleic --, therefor.

Signed and Sealed this
Second Day of August, 2011

David J. Kappos
*Director of the United States Patent and Trademark Office*

SEQUENCE LISTING

```
<160> NUMBER OF SEQ ID NOS: 4

<210> SEQ ID NO 1
<211> LENGTH: 29
<212> TYPE: RNA
<213> ORGANISM: Homo sapiens

<400> SEQUENCE: 1
aauauggauu gggauggagu ugcgcuaca                                         29

<210> SEQ ID NO 2
<211> LENGTH: 29
<212> TYPE: RNA
<213> ORGANISM: Homo sapiens

<400> SEQUENCE: 2
uuauaccuaa cccuaccuca acgcgaugu                                         29

<210> SEQ ID NO 3
<211> LENGTH: 13
<212> TYPE: RNA
<213> ORGANISM: Homo sapiens

<400> SEQUENCE: 3
guuaguagua uaa                                                          13

<210> SEQ ID NO 4
<211> LENGTH: 13
<212> TYPE: DNA
<213> ORGANISM: Artificial Sequence
<220> FEATURE:
<223> OTHER INFORMATION: Synthetic

<400> SEQUENCE: 4
ttatactact aac                                                          13
```